United States Patent
Ceccarelli et al.

(10) Patent No.: US 9,688,675 B2
(45) Date of Patent: *Jun. 27, 2017

(54) 1,7-NAPHTHYRIDINE DERIVATIVES

(71) Applicant: Hoffmann-La Roche Inc., Little Falls, NJ (US)

(72) Inventors: Simona M. Ceccarelli, Basel (CH); Ravi Jagasia, Loerrach (DE); Roland Jakob-Roetne, Inzlingen (DE); Jens-Uwe Peters, Grenzach-Wyhlen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,631

(22) Filed: Jan. 27, 2016

(65) Prior Publication Data

US 2016/0137643 A1 May 19, 2016

Related U.S. Application Data

(63) Continuation of application No. PCT/EP2014/066123, filed on Jul. 28, 2014.

(30) Foreign Application Priority Data

Jul. 29, 2013 (EP) .................................. 13178373

(51) Int. Cl.
- C07D 471/02 (2006.01)
- A61K 31/44 (2006.01)
- C07D 471/04 (2006.01)
- C07D 401/04 (2006.01)
- C07D 498/04 (2006.01)

(52) U.S. Cl.
CPC ......... C07D 471/04 (2013.01); C07D 401/04 (2013.01); C07D 498/04 (2013.01)

(58) Field of Classification Search
None
See application file for complete search history.

(56) References Cited

U.S. PATENT DOCUMENTS

2007/0078155 A1* 4/2007 Jaeschke .............. C07D 471/04
514/300

FOREIGN PATENT DOCUMENTS

| WO | WO 2008/046072 | * | 4/2008 |
| WO | WO 2009/155121 A2 | * | 12/2009 |
| WO | 2014/079787 A1 | | 5/2014 |
| WO | WO 2014/079787 A1 | * | 5/2014 |

OTHER PUBLICATIONS

Song, H. et al. Adult Neurogenesis in the Mammalian Brain: Significant Answers and Significant Questions. Neuron. 2011, 70(4), p. 687.*
Freshney, RI. Culture of Animal Cells: A Manual of Basic Technique. John Wiley and Sons. 2005, 5th Ed., p. 8.*
Kraus, KS. et al. Noise Trauma Impairs Neurogenesis in the Rat Hippocampus. Neuroscience. 2010, 167, p. 1216.*
International Search Report and Written Opinion for International Patent Application No. PCT/EP2014/066123, mailed Oct. 2, 2014, 4 pages.
MacMillan et al., "Development of Proneurogenic, Neuroprotective Small Molecules" JACS 43:10 (2011).
Piper et al., "P7C3 and an unbiased approach to drug discovery" Chem Soc Rev 43:11 (2014).

* cited by examiner

Primary Examiner — Noble Jarrell
Assistant Examiner — Ben S Michelson

(57) ABSTRACT

The present invention relates to compounds of general formula I wherein $R^1$, $R^2$, $R^3$ and $R^4$ are as defined herein which may be used for the treatment of schizophrenia, obsessive-compulsive

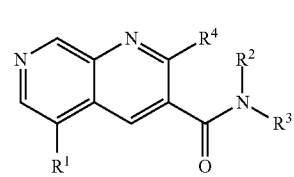

personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuroactive drugs, selected from alcohol, opiates, methamphetamine, phencyclidine and cocaine.

11 Claims, No Drawings

1,7-NAPHTHYRIDINE DERIVATIVES

CROSS REFERENCE TO RELATED APPLICATIONS

This application is a continuation of International Application No. PCT/EP2014/066123 having an international filing date of Jul. 28, 2014 and which claims benefit under 35 U.S.C. §119 to European Patent Application No. 13178373.0 filed Jul. 29, 2013. The entire contents of both are incorporated herein by reference.

FIELD OF THE INVENTION

The present invention relates to novel compounds of formula I, wherein $R^1$, $R^2$, $R^3$, and $R^4$ are as described herein, having pharmaceutical activity, their manufacture, pharmaceutical compositions containing them and their potential use as medicaments.

BACKGROUND OF THE INVENTION

Neurogenesis occurs in the developing and adult brain. Conceptually, the process of neurogenesis can be divided into four steps: (i) proliferation of neural stem cells (NSCs); (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyms of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyms, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

The stimulation of adult neurogenesis represents also a therapeutic target for optic neuropathy (S. Isenmann, A. Kretz, A. Cellerino, Progress in Retinal and Eye Research, 22, (2003) 483) and macular degeneration (G. Landa, O. Butovsky, J. Shoshani, M. Schwartz, A. Pollack, Current Eye Research 33, (2008) 1011).

Hence, chemical stimulation of adult neurogenesis offers new regenerative avenues and opportunities to develop novel drugs for treating neurological diseases and neuropsychiatric disorders.

Compounds that modulate neurogenesis may therefore be useful for treating of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine and cocaine.

The most preferred indications for compounds of formula I are Alzheimer's disease, depression, anxiety disorders and stroke.

BRIEF SUMMARY OF THE INVENTION

The present invention relates to compounds of general formula

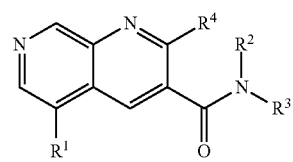

wherein
$R^1$ is phenyl or pyridinyl, which are optionally substituted by one, two or three substituents, selected from halogen, lower alkyl substituted by halogen, lower alkoxy, lower alkoxy substituted by halogen, cyano or $S(O)_2$-lower alkyl, or is morpholinyl, dihydropyranyl or piperidinyl, wherein piperidinyl is optionally substituted by halogen, or is C(O)O-lower alkyl;

$R^2$ is hydrogen;

$R^3$ is hydrogen, lower alkyl substituted by halogen, —$(CH_2)_n$—$S(O)_2$-lower alkyl, —$(CH_2)_n$-cycloalkyl or —$(CH_2)_n$-lower alkoxy;

$R^4$ is hydrogen or lower alkyl;

n is 0, 1 or 2;

or to a pharmaceutically acceptable acid addition salt, to a racemic mixture or to its corresponding enantiomer and/or optical isomers thereof.

A further object of the invention is a method for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, optic neuropathy or macular degeneration, abuse of neuro-active drugs, such as alcohol, opiates, methamphetamine, phencyclidine and cocaine, which method comprises administering an effective amount of a compound of formula I.

DETAILED DESCRIPTION OF THE INVENTION

The compounds that stimulate neurogenesis from neural stem cells (NSCs) have the potential to treat a variety of neurological conditions. One embodiment of the present invention is to provide compounds of Formula I wherein $R^1$, $R^2$, $R^3$ and $R^4$ are as defined in the Brief Summary of the Invention.

Another embodiment of the invention are compounds of formula I, wherein $R^1$ is phenyl or pyridinyl, which are optionally substituted by one, two or three sub stituents, selected from halogen, lower alkyl substituted by halogen, lower alkoxy, lower alkoxy substituted by halogen, cyano or $S(O)_2$-lower alkyl, for example the following compounds 5-(4-chlorophenyl)-1,7-naphthyridine-3-carboxamide
5-(4-(trifluoromethoxy)phenyl)-1,7-naphthyridine-3-carboxamide
5-(2-fluorophenyl)-1,7-naphthyridine-3-carboxamide
5-(3,4,5-trifluorophenyl)-1,7-naphthyridine-3-carboxamide
5-(4-fluorophenyl)-1,7-naphthyridine-3-carboxamide
5-(3,4-difluorophenyl)-1,7-naphthyridine-3-carboxamide
5-(2,4-difluorophenyl)-1,7-naphthyridine-3-carboxamide
5-(4-cyanophenyl)-1,7-naphthyridine-3-carboxamide
5-(4-(methylsulfonyl)phenyl)-1,7-naphthyridine-3-carboxamide
5-(4-(trifluoromethyl)phenyl)-1,7-naphthyridine-3-carboxamide
5-(4-chlorophenyl)-2-methyl-1,7-naphthyridine-3-carboxamide
5-(4-chloro-2-fluorophenyl)-1,7-naphthyridine-3-carboxamide
5-(4-chloro-2-fluorophenyl)-N-(2-(methylsulfonyl)ethyl)-1,7-naphthyridine-3-carboxamide
5-(2-fluorophenyl)-N-(2,2,2-trifluoroethyl)-1,7-naphthyridine-3-carboxamide
5-(2,4-difluorophenyl)-N-(2,2,2-trifluoroethyl)-1,7-naphthyridine-3-carboxamide
5-(4-fluorophenyl)-N-(2,2,2-trifluoroethyl)-1,7-naphthyridine-3-carboxamide
5-(4-chlorophenyl)-N-(4-(methylsulfonyl)benzyl)-1,7-naphthyridine-3-carboxamide
5-(4-chlorophenyl)-N-(3-(methylsulfonyl)benzyl)-1,7-naphthyridine-3-carboxamide
5-(4-chlorophenyl)-N-(cyclopropylmethyl)-1,7-naphthyridine-3-carboxamide
5-(4-chlorophenyl)-N-(2-methoxyethyl)-1,7-naphthyridine-3-carboxamide
5-(3-methoxyphenyl)-1,7-naphthyridine-3-carboxamide
5-(3-(trifluoromethoxy)phenyl)-1,7-naphthyridine-3-carboxamide
5-(6-chloropyridin-3-yl)-1,7-naphthyridine-3-carboxamide or
5-(2,4-dichlorophenyl)-1,7-naphthyridine-3-carboxamide.

Another embodiment of the invention are further compounds of formula I, wherein $R^1$ is morpholinyl, dihydropyranyl or piperidinyl, wherein piperidinyl is optionally substituted by halogen, for example 5-morpholino-1,7-naphthyridine-3-carboxamide
methyl 3-carbamoyl-1,7-naphthyridine-5-carboxylate
5-(3,6-dihydro-2H-pyran-4-yl)-1,7-naphthyridine-3-carboxamide or
5-(4,4-difluoropiperidin-1-yl)-1,7-naphthyridine-3-carboxamide.

Yet another embodiment of the invention are further compounds of formula I, wherein $R^2$ and $R^3$ are both hydrogen, for example the compounds 5-(4-chlorophenyl)-1,7-naphthyridine-3-carboxamide
5-(4-(trifluoromethoxy)phenyl)-1,7-naphthyridine-3-carboxamide
5-(2-fluorophenyl)-1,7-naphthyridine-3-carboxamide
5-(3,4,5-trifluorophenyl)-1,7-naphthyridine-3-carboxamide
5-(4-fluorophenyl)-1,7-naphthyridine-3-carboxamide
5-(3,4-difluorophenyl)-1,7-naphthyridine-3-carboxamide
5-(2,4-difluorophenyl)-1,7-naphthyridine-3-carboxamide
5-(4-cyanophenyl)-1,7-naphthyridine-3-carboxamide
5-(4-(methylsulfonyl)phenyl)-1,7-naphthyridine-3-carboxamide
5-(4-(trifluoromethyl)phenyl)-1,7-naphthyridine-3-carboxamide
5-(4-chlorophenyl)-2-methyl-1,7-naphthyridine-3-carboxamide
5-(4-chloro-2-fluorophenyl)-1,7-naphthyridine-3-carboxamide
5-morpholino-1,7-naphthyridine-3-carboxamide
5-(3-methoxyphenyl)-1,7-naphthyridine-3-carboxamide
5-(3-(trifluoromethoxy)phenyl)-1,7-naphthyridine-3-carboxamide
methyl 3-carbamoyl-1,7-naphthyridine-5-carboxylate
5-(3,6-dihydro-2H-pyran-4-yl)-1,7-naphthyridine-3-carboxamide
5-(4,4-difluoropiperidin-1-yl)-1,7-naphthyridine-3-carboxamide
5-(6-chloropyridin-3-yl)-1,7-naphthyridine-3-carboxamide or
5-(2,4-cichlorophenyl)-1,7-naphthyridine-3-carboxamide.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is $CF_3$.

The term "lower alkoxy substituted by halogen" denotes a lower alkoxy group as defined above, wherein at least one hydrogen atom is replaced by a halogen atom. The preferred group is $OCF_3$.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The present new compounds of formula I and their pharmaceutically acceptable salts can be prepared by methods known in the art, for example, by processes described below, which process comprises a) reacting a compound of formula

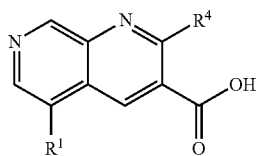

with a compound of formula $NHR^2R^3$2 to afford a compound of formula

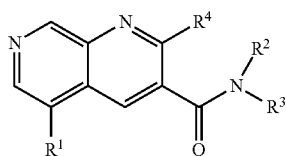

and, converting the compounds obtained into pharmaceutically acceptable acid addition salts, or b) reacting a compound of formula 3

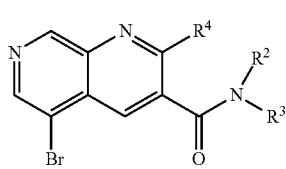

with a compound of formula

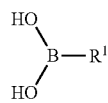

to a compound of formula

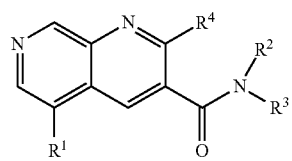

and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

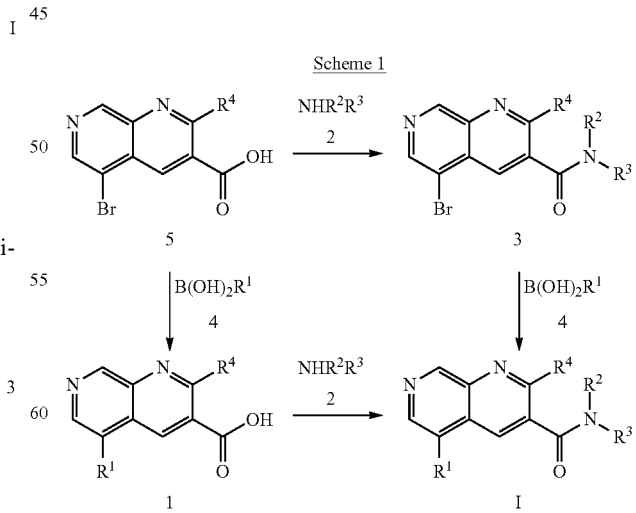

Scheme 1

A mixture of 5-bromo-1,7-naphthyridine-3-carboxylic acid of formula 5, N,N-diisopropylethylamine and O-(7- azabenzotriazol-1-yl)-N,N,N',N'-tetramethyluronium hexafluorophosphate (HATU) in dimethylformamide is stirred at room temperature for 10 minutes. The corresponding amine of formula 2 is added and stirring is continued over two day to yield a compound of formula 3.

Furthermore, to a suspension of 5-bromo-1,7-naphthyridine 3-carboxamide of formula 3 and a boronic acid of formula 4 and cesium carbonate in dioxane and water is added bis(diphenylphosphino)ferrocene-palladium(II)dichloride. The mixture is stirred at 80° C. for 3 hours. Removal of the solvent by distillation and chromatography yields the compound of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21'000 cells/cm$^2$ in a media volume of 38 μl.

4 hours after cell seeding, compound solutions are added at a volume of 2 μl. Stock solutions of the compounds (water, 5% DMSO) are diluted to obtain a dose response (11 points, dilution factor is 2), ranging from 8 μM to 8 nM. Controls are run to consistently determine the neurogenic properties of the cells:

Negative (neutral) control is cell culture Media (final DMSO concentration: 0.25%).

Positive controls are:

1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The $EC_{150}$ is the compound concentration at which 150% activity of control (100%) is reached. The preferred compounds show a $EC_{150}$ (μM) in the range of <2.5 μM as shown in Table 1 below.

TABLE 1
List of examples and EC$_{150}$ data of novel compounds
| Example | Structure | Name | EC$_{150}$ (uM) |
|---|---|---|---|
| 1 | 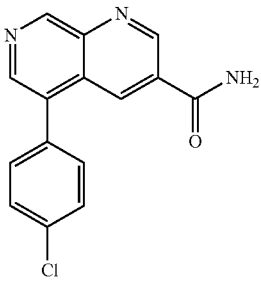 | 5-(4-Chlorophenyl)-1,7-naphthyridine-3-carboxamide | 0.09 |
| 2 | 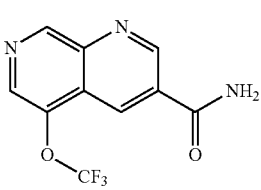 [SMILES: NC(=O)c1cnc2cncc(OC(F)(F)F)c2c1] | 5-(4-(Trifluoromethoxy)phenyl)-1,7-naphthyridine-3-carboxamide | 0.47 |
| 3 | 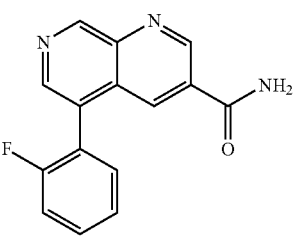 [SMILES: NC(=O)c1cnc2cncc(-c3ccccc3F)c2c1] | 5-(2-Fluorophenyl)-1,7-naphthyridine-3-carboxamide | 1.12 |
| 4 | 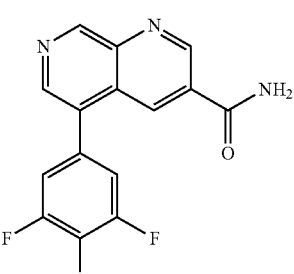 | 5-(3,4,5-Trifluorophenyl)-1,7-naphthyridine-3-carboxamide | 1.90 |
| 5 | 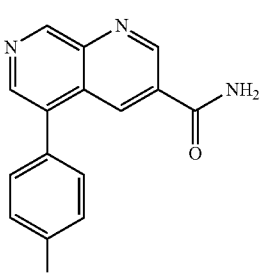 | 5-(4-Fluorophenyl)-1,7-naphthyridine-3-carboxamide | 1.10 |

TABLE 1-continued
List of examples and EC$_{150}$ data of novel compounds
| Example | Structure | Name | EC$_{150}$ (uM) |
|---|---|---|---|
| 6 | 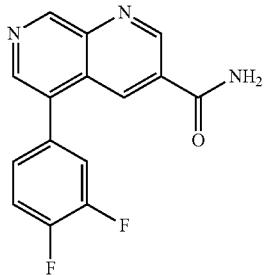 | 5-(3,4-Difluorophenyl)-1,7-naphthyridine-3-carboxamide | 0.55 |
| 7 | 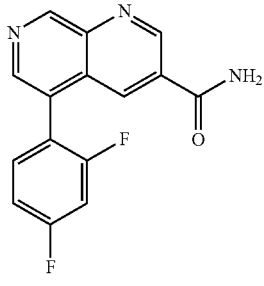 [SMILES: NC(=O)c1cnc2cncc(-c3ccc(F)cc3F)c2c1] | 5-(2,4-Difluorophenyl)-1,7-naphthyridine-3-carboxamide | 0.48 |
| 8 | 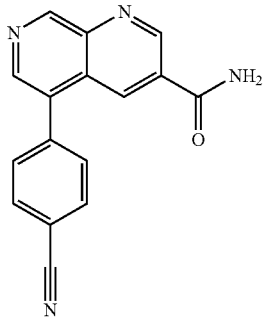 [SMILES: N#Cc1ccc(-c2cncc3ncc(C(N)=O)cc23)cc1] | 5-(4-Cyanophenyl)-1,7-naphthyridine-3-carboxamide | 1.37 |
| 9 | 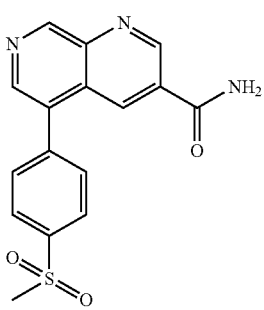 [SMILES: CS(=O)(=O)c1ccc(-c2cncc3ncc(C(N)=O)cc23)cc1] | 5-(4-(Methylsulfonyl)phenyl)-1,7-naphthyridine-3-carboxamide | 1.58 |

TABLE 1-continued

List of examples and EC$_{150}$ data of novel compounds

| Example | Structure | Name | EC$_{150}$ (uM) |
|---|---|---|---|
| 10 | 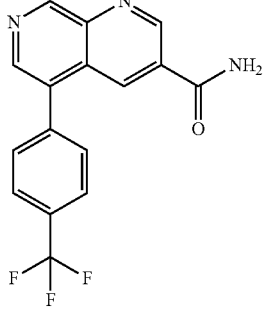 | 5-(4-(Trifluoromethyl)phenyl)-1,7-naphthyridine-3-carboxamide | 0.30 |
| 11 | 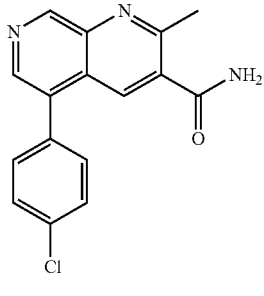 [SMILES: Cc1nc2cncc(-c3ccc(Cl)cc3)c2cc1C(N)=O] | 5-(4-Chlorophenyl)-2-methyl-1,7-naphthyridine-3-carboxamide | 0.12 |
| 12 | 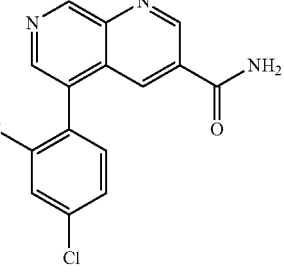 | 5-(4-Chloro-2-fluorophenyl)-1,7-naphthyridine-3-carboxamide | 0.07 |
| 13 | 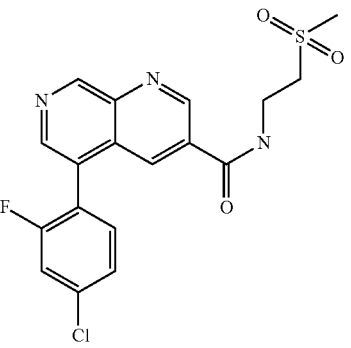 [SMILES: CS(=O)(=O)CCNC(=O)c1cnc2cncc(-c3ccc(Cl)cc3F)c2c1] | 5-(4-Chloro-2-fluorophenyl)-N-(2-(methylsulfonyl)ethyl)-1,7-naphthyridine-3-carboxamide | 1.51 |
| 14 | 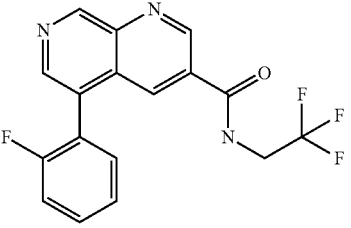 [SMILES: O=C(NCC(F)(F)F)c1cnc2cncc(-c3ccccc3F)c2c1] | 5-(2-Fluorophenyl)-N-(2,2,2-trifluoroethyl)-1,7-naphthyridine-3-carboxamide | 1.21 |

TABLE 1-continued

List of examples and EC$_{150}$ data of novel compounds

| Example | Structure | Name | EC$_{150}$ (uM) |
|---|---|---|---|
| 15 | 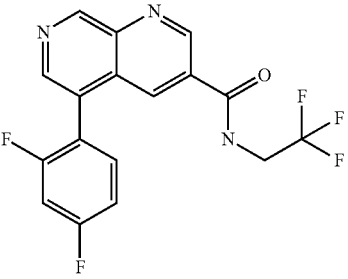 [SMILES: O=C(NCC(F)(F)F)c1cnc2cncc(-c3ccc(F)cc3F)c2c1] | 5-(2,4-Difluorophenyl)-N-(2,2,2-trifluoroethyl)-1,7-naphthyridine-3-carboxamide | 1.36 |
| 16 | 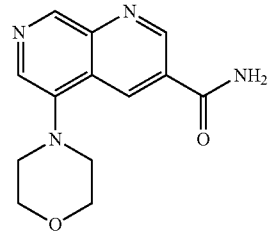 [SMILES: NC(=O)c1cnc2cncc(N3CCOCC3)c2c1] | 5-Morpholino-1,7-naphthyridine-3-carboxamide | 1.43 |
| 17 | 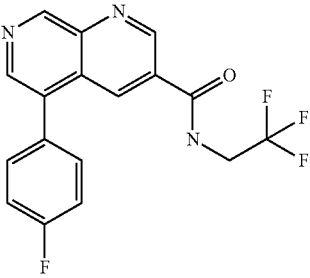 [SMILES: O=C(NCC(F)(F)F)c1cnc2cncc(-c3ccc(F)cc3)c2c1] | 5-(4-Fluorophenyl)-N-(2,2,2-trifluoroethyl)-1,7-naphthyridine-3-carboxamide | 1.13 |
| 18 | 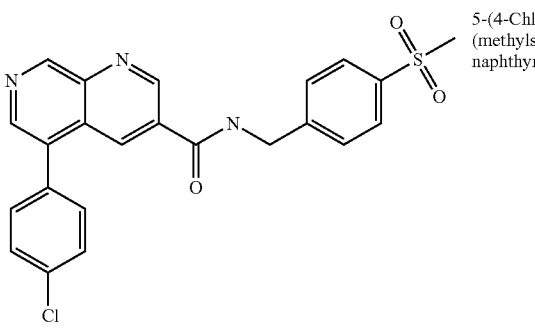 | 5-(4-Chlorophenyl)-N-(4-(methylsulfonyl)benzyl)-1,7-naphthyridine-3-carboxamide | 0.25 |
| 19 | 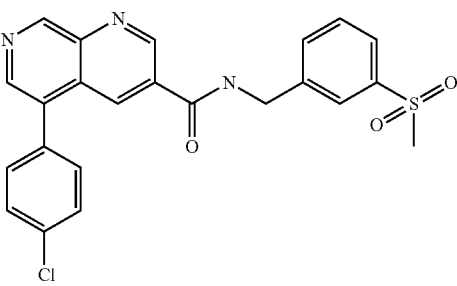 [SMILES: CS(=O)(=O)c1cccc(CNC(=O)c2cnc3cncc(-c4ccc(Cl)cc4)c3c2)c1] | 5-(4-Chlorophenyl)-N-(3-(methylsulfonyl)benzyl)-1,7-naphthyridine-3-carboxamide | 3.18 |

TABLE 1-continued

List of examples and EC$_{150}$ data of novel compounds

| Example | Structure | Name | EC$_{150}$ (uM) |
|---|---|---|---|
| 20 | 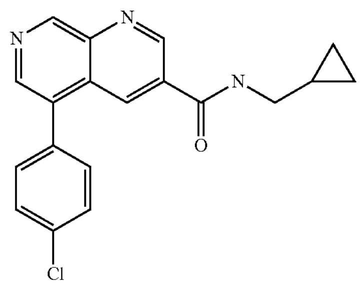 [SMILES: O=C(NCC1CC1)c1cnc2cncc(-c3ccc(Cl)cc3)c2c1] | 5-(4-Chlorophenyl)-N-(cyclopropylmethyl)-1,7-naphthyridine-3-carboxamide | 4.24 |
| 21 | 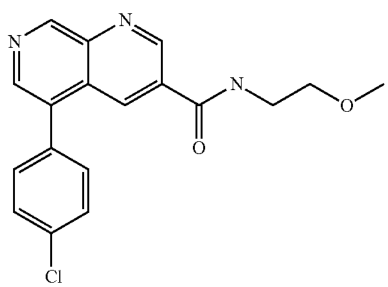 [SMILES: COCCNC(=O)c1cnc2cncc(-c3ccc(Cl)cc3)c2c1] | 5-(4-Chlorophenyl)-N-(2-methoxyethyl)-1,7-naphthyridine-3-carboxamide | 4.60 |
| 22 | 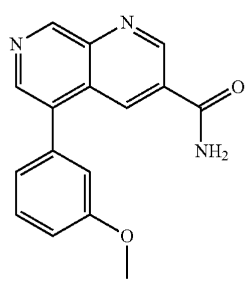 [SMILES: COc1cccc(-c2cncc3ncc(C(N)=O)cc23)c1] | 5-(3-Methoxyphenyl)-1,7-naphthyridine-3-carboxamide | 1.93 |
| 23 | 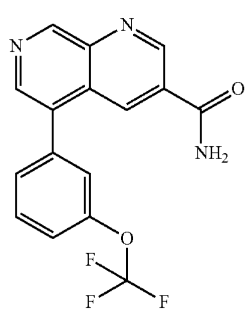 [SMILES: NC(=O)c1cnc2cncc(-c3cccc(OC(F)(F)F)c3)c2c1] | 5-(3-(Trifluoromethoxy)phenyl)-1,7-naphthyridine-3-carboxamide | 5.73 |
| 24 | 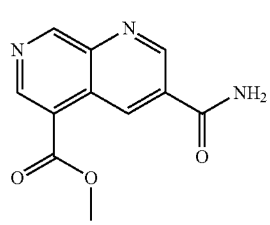 [SMILES: COC(=O)c1cncc2ncc(C(N)=O)cc12] | Methyl 3-carbamoyl-1,7-naphthyridine-5-carboxylate | 3.20 |

TABLE 1-continued

List of examples and EC$_{150}$ data of novel compounds

| Example | Structure | Name | EC$_{150}$ (uM) |
|---|---|---|---|
| 25 | 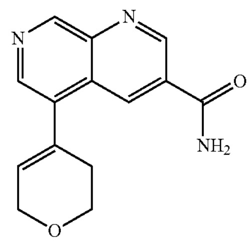 [SMILES: NC(=O)c1cnc2cncc(C3=CCOCC3)c2c1] | 5-(3,6-Dihydro-2H-pyran-4-yl)-1,7-naphthyridine-3-carboxamide | 4.41 |
| 26 | 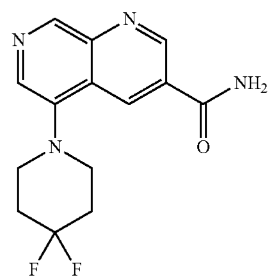 [SMILES: NC(=O)c1cnc2cncc(N3CCC(F)(F)CC3)c2c1] | 5-(4,4-Difluoropiperidin-1-yl)-1,7-naphthyridine-3-carboxamide | 2.09 |
| 27 | 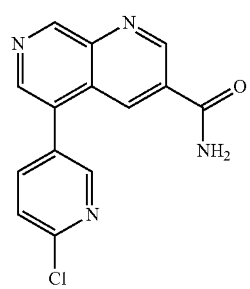 [SMILES: NC(=O)c1cnc2cncc(-c3ccc(Cl)nc3)c2c1] | 5-(6-Chloropyridin-3-yl)-1,7-naphthyridine-3-carboxamide | 1.08 |
| 28 | 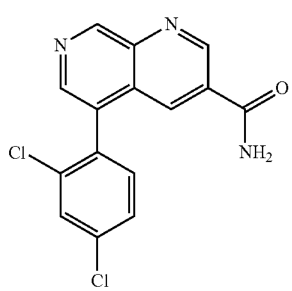 [SMILES: NC(=O)c1cnc2cncc(-c3ccc(Cl)cc3Cl)c2c1] | 5-(2,4-Dichlorophenyl)-1,7-naphthyridine-3-carboxamide | 0.46 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragés, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragés and hard gelatine capsules.

Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

|  |  | mg/tablet | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1

5-(4-Chlorophenyl)-1,7-naphthyridine-3-carboxamide

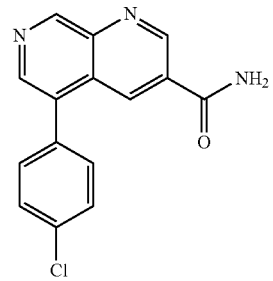 [SMILES: NC(=O)c1cnc2cncc(-c3ccc(Cl)cc3)c2c1]

a) Ethyl 5-bromo-1,7-naphthyridine-3-carboxylate

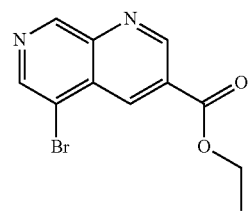 [SMILES: CCOC(=O)c1cnc2cncc(Br)c2c1]

Ethyl-1,7-naphthyridine-3-carboxylate (CAS949922-44-5, 50.0 mg, 247 μmol) and N-bromosuccinimide (52.8 mg, 297 μmol) in acetic acid (3 ml) were stirred at 80° C. for 1 hour. The crude reaction mixture was concentrated in vacuo and purified by chromatography (silica gel, ethyl acetate/heptane=30:70 to 100:0) to yield the title compound as light brown solid (62 mg, 89%). MS: m/e=281.2, 283.3 [M+H]$^+$.

b) Ethyl 5-(4-chlorophenyl)-1,7-naphthyridine-3-carboxylate

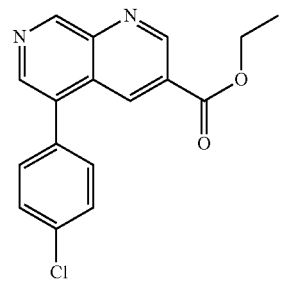 [SMILES: CCOC(=O)c1cnc2cncc(-c3ccc(Cl)cc3)c2c1]

To a suspension of ethyl-5-bromo-1,7-naphthyridine-3-carboxylate (55 mg, 196 μmol) and 4-chlorophenylboronic acid (30.6 mg, 196 μmol) and cesium carbonate (70.1 mg, 215 μmol) in dioxane (5 ml) and water (0.5 ml) was added bis(diphenylphosphino)ferrocene-palladium(II)dichloride (7.16 mg, 9.78 μmol). The mixture was stirred at 80° C. for 2 hours. Removal of the solvent by distillation and chromatography (silica gel, ethyl acetate/heptane=20:80 to 100:0)

and trituration with diethyl ether/pentane yielded the title compound as light brown solid (54 mg, 88%). MS: m/e=313.4 [M+H]+.

c) 5-(4-Chlorophenyl)-1,7-naphthyridine-3-carboxylic acid

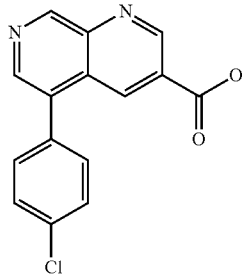 [SMILES: NC(=O)c1cnc2cncc(-c3ccc(Cl)cc3)c2c1]

Ethyl-5-(4-chlorophenyl)-1,7-naphthyridine-3-carboxylate (50 mg, 160 µmol) was combined with dioxane (6 ml) to give a light brown solution. Lithiumhydroxide (4.59 mg, 192 µmol) in water (1 ml) was added and the mixture was stirred at room temperature for 3 hours. The crude reaction mixture was concentrated in vacuo, poured into water (10 ml), acidified with 2N aqueous hydrochloric acid and extracted with ethyl acetate to yield the title compound as light brown solid (24 mg, 53%). MS: m/e=285.4 [M+H]+.

d) 5-(4-Chlorophenyl)-1,7-naphthyridine-3-carboxamide

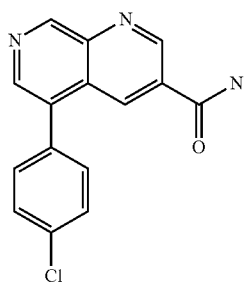

A mixture of 5-(4-chlorophenyl)-1,7-naphthyridine-3-carboxylic acid (240 mg, 843 µmol), 1,1'-carbonyldiimidazole (137 mg, 843 µmol) in dichloromethane (40 ml) was stirred at room temperature for 1 hour. Aqueous ammonium hydroxide (25%, 40 ml, 1.03 mol) was added and stirring was continued for 1 hour. Extraction with water/dichloromethane and chromatography ethyl acetate/heptane=50: 50 to 100:0) yielded the title compound as light yellow solid (55 mg, 23%). MS: m/e=284.5 [M+H]+.

EXAMPLE 2

5-(4-(Trifluoromethoxy)phenyl)-1,7-naphthyridine-3-carboxamide

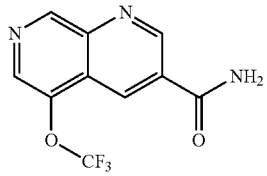

a) 5-Bromo-1,7-naphthyridine-3-carboxylic acid

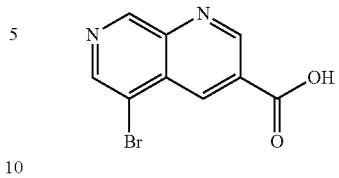

Ethyl-5-bromo-1,7-naphthyridine-3-carboxylate (1.893 g, 6.73 mmol) was combined with dioxane (100 ml) to give a light brown solution. Lithiumhydroxide (194 mg, 8.08 mmol) in water (16.7 ml) was added and the mixture was stirred at room temperature overnight. The crude reaction mixture was concentrated in vacuo and poured into water. The mixture was acidified with 2N aqueous hydrochloric acid. The precipitate was filtered and dried to yield the title compound as light brown solid (1.55 g, 91%). MS: m/e=253.4, 255.3 [M+H]+.

b) 5-Bromo-1,7-naphthyridine-3-carboxamide

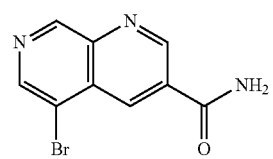 [SMILES: NC(=O)c1cnc2cncc(Br)c2c1]

A mixture of 5-bromo-1,7-naphthyridine-3-carboxylic acid (1.00 g, 3.95 mmol), 1,1'-carbonyldiimidazole (641 mg, 3.95 mmol) in dichloromethane (188 ml) was stirred at room temperature for 1 hour. Aqueous ammonium hydroxide (25%, 143 ml, 3.7 mol) was added and stirring was continued for 2 hours. Extraction with water/dichloromethane and trituration with methanol (0.5 ml) yielded the title compound as off-white solid (435 mg, 44%). MS: m/e=252.4, 254.4 [M+H]+.

c) 5-(4-(Trifluoromethoxy)phenyl)-1,7-naphthyridine-3-carboxamide

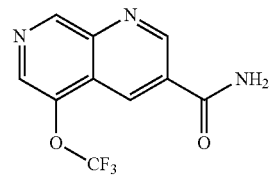 [SMILES: NC(=O)c1cnc2cncc(OC(F)(F)F)c2c1]

To a suspension of 5-bromo-1,7-naphthyridine-3-carboxamide (40 mg, 159 µmol) and 4-(trifluoromethoxy)phenylboronic acid (32.7 mg, 159 µmol) and cesium carbonate (56.9 mg, 175 mol) in dioxane (5 ml) and water (0.6 ml) was added bis(diphenylphosphino)ferrocene-palladium(II)dichloride (5.81 mg, 7.93 µmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (25 mg, 47%). MS: m/e=334.4 [M+H]+.

EXAMPLE 3

5-(2-Fluorophenyl)-1,7-naphthyridine-3-carboxamide

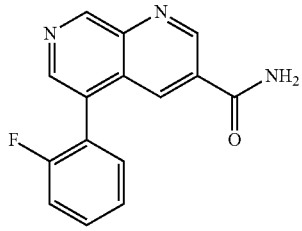 [SMILES: NC(=O)c1cnc2cncc(-c3ccccc3F)c2c1]

To a suspension of 5-bromo-1,7-naphthyridine-3-carboxamide (40 mg, 159 μmol) and 2-fluorophenylboronic acid (22.2 mg, 159 μmol) and cesium carbonate (56.9 mg, 175 μmol) in dioxane (5 ml) and water (0.6 ml) was added bis(diphenylphosphino)ferrocene-palladium(II)dichloride (5.81 mg, 7.93 μmol). The mixture was stirred at 80° C. for 2 hours. Removal of the solvent by distillation and chromatography (silica gel, ethyl acetate/heptane=50:50 to 100:0) and trituration with diethyl ether yielded the title compound as light brown solid (40 mg, 94%). MS: m/e=268.4 [M+H]$^+$.

EXAMPLE 4

5-(3,4,5-Trifluorophenyl)-1,7-naphthyridine-3-carboxamide

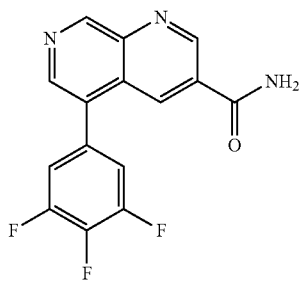 [SMILES: NC(=O)c1cnc2cncc(-c3cc(F)c(F)c(F)c3)c2c1]

To a suspension of 5-bromo-1,7-naphthyridine-3-carboxamide (40 mg, 159 μmol) and 3,4,5-trifluorophenylboronic acid (27.9 mg, 159 μmol) and cesium carbonate (56.9 mg, 175 μmol) in dioxane (5 ml) and water (0.5 ml) was added bis(diphenylphosphino)ferrocene-palladium(II)dichloride (5.81 mg, 7.93 μmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (25 mg, 52%). MS: m/e=304.4[M+H]$^+$.

EXAMPLE 5

5-(4-Fluorophenyl)-1,7-naphthyridine-3-carboxamide

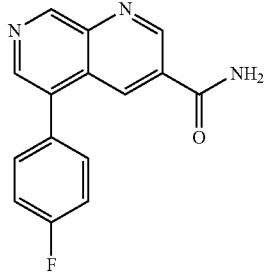 [SMILES: NC(=O)c1cnc2cncc(-c3ccc(F)cc3)c2c1]

To a suspension of 5-bromo-1,7-naphthyridine-3-carboxamide (40 mg, 159 μmol) and 4-fluorophenylboronic acid (22.2 mg, 159 μmol) and cesium carbonate (56.9 mg, 175 μmol) in dioxane (5 ml) and water (0.6 ml) was added bis(diphenylphosphino)ferrocene-palladium(II)dichloride (5.81 mg, 7.93 μmol). The mixture was stirred at 80 ° C. for 2 hours. Removal of the solvent by distillation and chromatography (silica gel, ethyl acetate/heptane=50:50 to 100:0) and trituration with diethyl ether yielded the title compound as off-white solid (29 mg, 68%). MS: m/e=268.4 [M+H]$^+$.

EXAMPLE 6

5-(3,4-Difluorophenyl)-1,7-naphthyridine-3-carboxamide

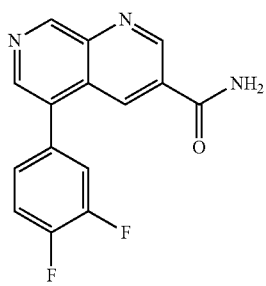 [SMILES: NC(=O)c1cnc2cncc(-c3ccc(F)c(F)c3)c2c1]

To a suspension of 5-bromo-1,7-naphthyridine-3-carboxamide (40 mg, 159 μmol) and 3,4-difluorophenylboronic acid (25.1 mg, 159 μmol) and cesium carbonate (56.9 mg, 175 μmol) in dioxane (5 ml) and water (0.6 ml) was added bis(diphenylphosphino)ferrocene-palladium(II)dichloride (5.81 mg, 7.93 μmol). The mixture was stirred at 80 ° C. for 2 hours. Removal of the solvent by distillation and chromatography (silica gel, ethyl acetate/heptane=50:50 to 100:0) and trituration with diethyl ether yielded the title compound as off-white solid (35 mg, 77%). MS: m/e=286.4 [M+H]$^+$.

EXAMPLE 7

5-(2,4-Difluorophenyl)-1,7-naphthyridine-3-carboxamide

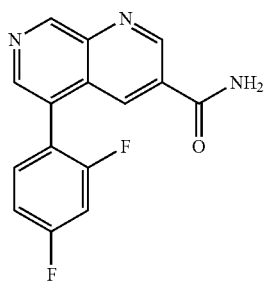 [SMILES: NC(=O)c1cnc2cncc(-c3ccc(F)cc3F)c2c1]

To a suspension of 5-bromo-1,7-naphthyridine-3-carboxamide (40 mg, 159 µmol) and 2,4-difluorophenylboronic acid (25.1 mg, 159 µmol) and cesium carbonate (56.9 mg, 175 µmol) in dioxane (5 ml) and water (0.6 ml) was added bis(diphenylphosphino)ferrocene-palladium(II)dichloride (5.81 mg, 7.93 µmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (42 mg, 93%). MS: m/e=286.4 [M+H]$^+$.

EXAMPLE 8

5-(4-Cyanophenyl)-1,7-naphthyridine-3-carboxamide

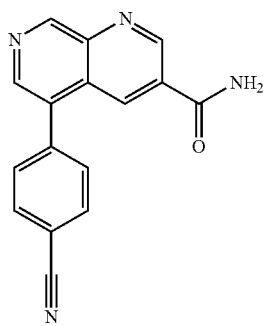 [SMILES: N#Cc1ccc(-c2cncc3ncc(C(N)=O)cc23)cc1]

To a suspension of 5-bromo-1,7-naphthyridine-3-carboxamide (40 mg, 159 µmol) and 4-cyanophenylboronic acid (23.3 mg, 159 µmol) and cesium carbonate (56.9 mg, 175 µmol) in dioxane (5 ml) and water (0.6 ml) was added bis(diphenylphosphino)ferrocene-palladium(II)dichloride (5.81 mg, 7.93 µmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (25 mg, 57%). MS: m/e=275.4[M+H]$^+$.

EXAMPLE 9

5-(4-(Methylsulfonyl)phenyl)-1,7-naphthyridine-3-carboxamide

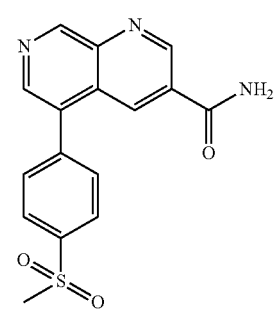 [SMILES: CS(=O)(=O)c1ccc(-c2cncc3ncc(C(N)=O)cc23)cc1]

To a suspension of 5-bromo-1,7-naphthyridine-3-carboxamide (40 mg, 159 µmol) and 4-(methylsulfonyl)phenylboronic acid (31.7 mg, 159 µmol) and cesium carbonate (56.9 mg, 175 µmol) in dioxane (5 ml) and water (0.6 ml) was added bis(diphenylphosphino)ferrocene-palladium(II)dichloride (5.81 mg, 7.93 µmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (37 mg, 71%). MS: m/e=328.4 [M+H]$^+$.

EXAMPLE 10

5-(4-(Trifluoromethyl)phenyl)-1,7-naphthyridine-3-carboxamide

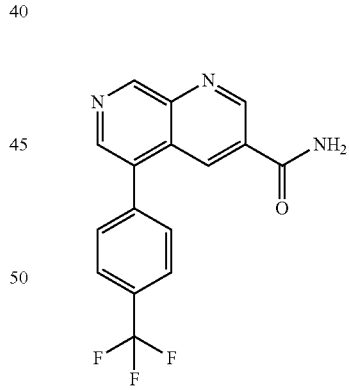

To a suspension of 5-bromo-1,7-naphthyridine-3-carboxamide (20 mg, 79.3 µmol) and 4-(trifluoromethyl)phenylboronic acid (15.1 mg, 79.3 µmol) and cesium carbonate (28.4 mg, 87.3 µmol) in dioxane (5 ml) and water (0.5 ml) was added bis(diphenylphosphino)ferrocene-palladium(II) dichloride (2.9 mg, 3.97 µmol). The mixture was stirred at 80° C. for 2 hours. Removal of the solvent by distillation and chromatography (silica gel, ethyl acetate/heptane=50:50 to 100:0) and trituration with diethyl ether yielded the title compound as off-white solid (18 mg, 72%). MS: m/e=318.4 [M+H]$^+$.

EXAMPLE 11

5-(4-Chlorophenyl)-2-methyl-1,7-naphthyridine-3-carboxamide

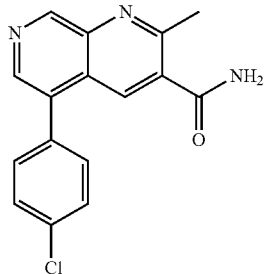 [SMILES: Cc1nc2cncc(-c3ccc(Cl)cc3)c2cc1C(N)=O]

a) Ethyl-5-bromo-2-methyl-1,7-naphthyridine-3-carboxylate

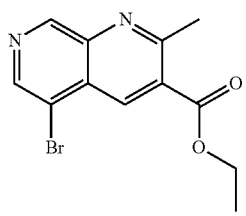 [SMILES: CCOC(=O)c1cc2c(Br)cncc2nc1C]

Ethyl-2-methyl-1,7-naphthyridine-3-carboxylate (CAS55234-62-3, 760 mg, 3.51 mmol) and N-bromosuccinimide (751 mg, 4.22 mmol) in acetic acid (50 ml) was heated at 80° C. for 2 hours. The crude reaction mixture was concentrated in vacuo and purified by chromatography (silica gel, ethyl acetate/heptane=0:100 to 50:50) to yield the title compound as off-white solid (266 mg, 26%). MS: m/e=295.3, 297.3 [M+H]$^+$.

b) 5-Bromo-2-methyl-1,7-naphthyridine-3-carboxylic acid

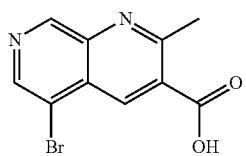

Ethyl-5-bromo-2-methyl-1,7-naphthyridine-3-carboxylate (260 mg, 881 μmol) was combined with dioxane (30 ml) to give a light brown solution. Lithiumhydroxide (25.3 mg, 1.06 mmol) in water (5 ml) was added and the mixture was stirred at room temperature for 4 days. The crude reaction mixture was concentrated in vacuo, poured into water (10 ml), acidified with 2N aqueous hydrochloric acid. The precipitate was filtered and dried in vacuo to yield the title compound as off white solid (215 mg, 91%). MS: m/e=267.3, 269.2[M+H]$^+$.

c) 5-Bromo-2-methyl-1,7-naphthyridine-3-carboxamide

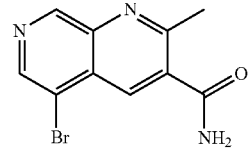

A mixture of 5-bromo-2-methyl-1,7-naphthyridine-3-carboxylic acid (210 mg, 786 μmol), 1,1'-carbonyldiimidazole (127 mg, 786 μmol) in dichloromethane (10 ml) was stirred at room temperature for 1 hour. Aqueous ammonium hydroxide (25%, 3.0 ml, 77 mol) was added and stirring was continued for 1 hour. Extraction with water/dichloromethane yielded the title compound as off-white solid (154 mg, 74%). MS: m/e=266.3, 268.3 [M+H]$^+$.

d) 5-(4-Chlorophenyl)-2-methyl-1,7-naphthyridine-3-carboxamide

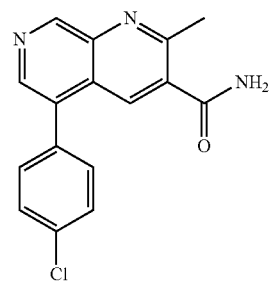 [SMILES: Cc1nc2cncc(-c3ccc(Cl)cc3)c2cc1C(N)=O]

To a suspension of 5-bromo-2-methyl-1,7-naphthyridine-3-carboxamide (100 mg, 376 μmol) and 4-chlorophenylboronic acid (58.8 mg, 376 μmol) and cesium carbonate (135 mg, 413 μmol) in dioxane (15 ml) and water (1.5 ml) was added bis(diphenylphosphino)ferrocene-palladium(II)dichloride (13.7 mg, 18.8 μmol). The mixture was stirred at 80° C. for 2 hours. Removal of the solvent by distillation and chromatography (silica gel, ethyl acetate/heptane=20:80 to 100:0) and trituration with diethyl ether yielded the title compound as off-white solid (69 mg, 62%). MS: m/e=298.4 [M+H]$^+$.

EXAMPLE 12

5-(4-Chloro-2-fluorophenyl)-1,7-naphthyridine-3-carboxamide

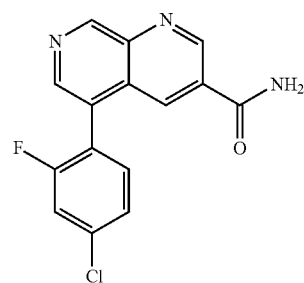 [SMILES: NC(=O)c1cnc2cncc(-c3ccc(Cl)cc3F)c2c1]

To a suspension of 5-bromo-1,7-naphthyridine-3-carboxamide (40 mg, 159 μmol) and 4-chloro-2-fluorophenylboronic acid (27.7 mg, 159 μmol) and cesium carbonate (56.9 mg, 175 μmol) in dioxane (5 ml) and water (0.6 ml) was added bis(diphenylphosphino)ferrocene-palladium(II)dichloride (5.81 mg, 7.93 μmol). The mixture was stirred at 80 ° C. for 2 hours. Removal of the solvent by distillation and chromatography (silica gel, ethyl acetate/heptane=20:80 to 100:0) and trituration with diethyl ether/pentane yielded the title compound as off-white solid (41 mg, 86%). MS: m/e=302.4 [M+H]$^+$.

EXAMPLE 13

5-(4-Chloro-2-fluorophenyl)-N-(2-(methylsulfonyl)ethyl)-1,7-naphthyridine-3-carboxamide

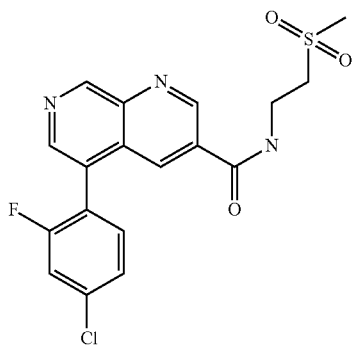 [SMILES: CS(=O)(=O)CCNC(=O)c1cnc2cncc(-c3ccc(Cl)cc3F)c2c1]

a) 5-Bromo-N-(2-(methylsulfonyl)ethyl)-1,7-naphthyridine-3-carboxamide

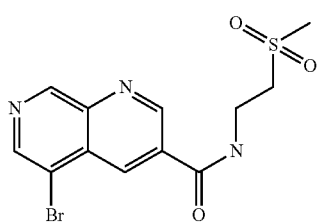 [SMILES: CS(=O)(=O)CCNC(=O)c1cnc2cncc(Br)c2c1]

5-Bromo-1,7-naphthyridine-3-carboxylic acid (500 mg, 1.98 mmol) in dichloromethane (30 ml) was combined with 3 drops of dimethylformamide. Under cooling oxalyl chloride (2.51 g, 1.73 ml, 19.8 mmol) was added slowly. The mixture was stirred for 30 minutes at 0 ° C. and for 30 minutes at room temperature. The crude reaction mixture was concentrated in vacuo. It was taken up in dichloromethane (30 ml) and was added at 0 ° C. to a mixture of 2-(methylsulfonyl)ethanamine hydrochloride (315 mg, 1.98 mmol) and triethylamine (420 mg, 578 μl, 4.15 mmol) in dichloromethane (30 ml). The mixture was stirred for 30 minutes at 0 ° C. and then at room temperature for 2 hours. Extraction with dichloromethane/water and trituration with ethyl acetate (5 ml) yielded the title compound as light brown solid (470 mg, 66%). MS: m/e=358.4, 360.4 [M+H]$^+$.

b) 5-(4-Chloro-2-fluorophenyl)-N-(2-(methylsulfonyl)ethyl)-1,7-naphthyridine-3-carboxamide

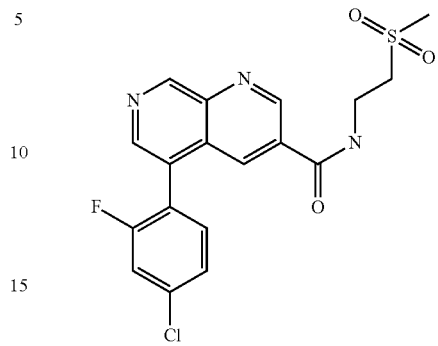

To a suspension of 5-bromo-N-(2-(methylsulfonyl)ethyl)-1,7-naphthyridine-3-carboxamide (100 mg, 279 μmol) and 4-chloro-2-fluorophenylboronic acid (48.7 mg, 279 μmol) and cesium carbonate (100 mg, 307 μmol) in dioxane (10 ml) and water (1 ml) was added bis(diphenylphosphino)ferrocene-palladium(II)dichloride (10.2 mg, 14.0 μmol). The mixture was stirred at 80 ° C. for 2 hours. Removal of the solvent by distillation and chromatography (silica gel, ethyl acetate/heptane=50:50 to 100:0) and trituration with diethyl ether/pentane yielded the title compound as off-white solid (60 mg, 53%). MS: m/e=408.4 [M+H]$^+$.

EXAMPLE 14

5-(2-Fluorophenyl)-N-(2,2,2-trifluoroethyl)-1,7-naphthyridine-3-carboxamide

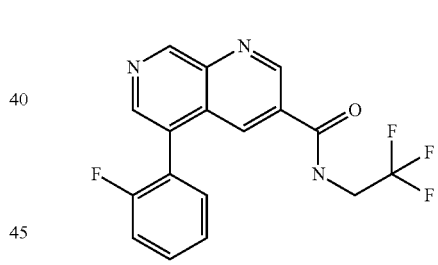

a) 5-Bromo-N-(2,2,2-trifluoroethyl)-1,7-naphthyridine-3-carboxamide

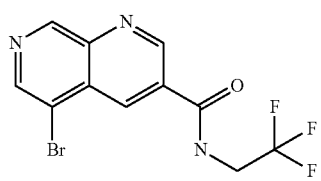 [SMILES: O=C(NCC(F)(F)F)c1cnc2cncc(Br)c2c1]

5-Bromo-1,7-naphthyridine-3-carboxylic acid (300 mg, 1.19 mmol) in dichloromethane (20 ml) was combined with 3 drops of dimethylformamide. Under cooling oxalyl chloride (752 mg, 519 μl, 5.93 mmol) was added slowly. The mixture was stirred for 30 minutes at 0 ° C. and for 30 minutes at room temperature. The crude reaction mixture was concentrated in vacuo. It was taken up in dichloromethane (30 ml) and was added at 0 ° C. to a mixture of 2,2,2-trifluoroethanamine (117 mg, 1.19 mmol) and triethylamine (252 mg, 347 μl, 2.49 mmol) in dichloromethane (20 ml). The mixture was stirred for 30 minutes at 0 °C. and then at room temperature for 1 hour. Extraction with dichloromethane/water and chromatography (silica gel, ethyl acetate/heptane=50:50 to 100:0) yielded the title compound as light brown solid (230 mg, 58%). MS: m/e=334.3, 336.3 [M+H]$^+$.

b) 5-(2-Fluorophenyl)-N-(2,2,2-trifluoroethyl)-1,7-naphthyridine-3-carboxamide

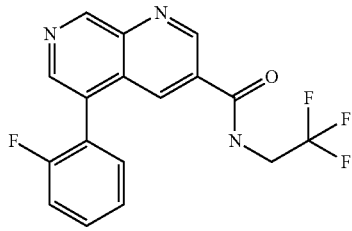 [SMILES: O=C(NCC(F)(F)F)c1cnc2cncc(-c3ccccc3F)c2c1]

To a suspension of 5-bromo-N-(2,2,2-trifluoroethyl)-1,7-naphthyridine-3-carboxamide (100 mg, 299 μmol) and 2-fluorophenylboronic acid (41.9 mg, 299 μmol) and cesium carbonate (107 mg, 329 μmol) in dioxane (15 ml) and water (1.5 ml) was added bis(diphenylphosphino)ferrocene-palladium(II)dichloride (11.0 mg, 15.0 μmol). The mixture was stirred at 80 °C. for 2 hours. Removal of the solvent by distillation and chromatography (silica gel, ethyl acetate/heptane=50:50 to 100:0) and trituration with diethyl ether/pentane yielded the title compound as off-white solid (101 mg, 97%). MS: m/e=350.4 [M+H]$^+$.

EXAMPLE 15

5-(2,4-Difluorophenyl)-N-(2,2,2-trifluoroethyl)-1,7-naphthyridine-3-carboxamide

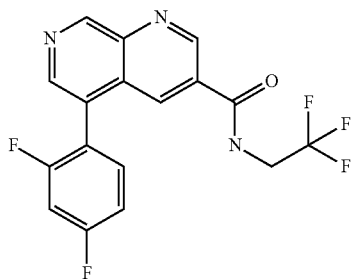 [SMILES: O=C(NCC(F)(F)F)c1cnc2cncc(-c3ccc(F)cc3F)c2c1]

To a suspension of 5-bromo-N-(2,2,2-trifluoroethyl)-1,7-naphthyridine-3-carboxamide (100 mg, 299 μmol) and 2,4-difluorophenylboronic acid (47.3 mg, 299 μmol) and cesium carbonate (107 mg, 329 μmol) in dioxane (15 ml) and water (1.5 ml) was added bis(diphenylphosphino)ferrocene-palladium(II)dichloride (11.0 mg, 15.0 μmol). The mixture was stirred at 80 °C. for 3 hours. Removal of the solvent by distillation and chromatography (silica gel, ethyl acetate/heptane=50:50 to 100:0) and trituration with diethyl ether/pentane yielded the title compound as off-white solid (86 mg, 78%). MS: m/e=368.4 [M+H]$^+$.

EXAMPLE 16

5-Morpholino-1,7-naphthyridine-3-carboxamide

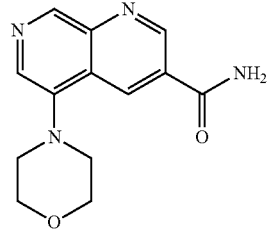 [SMILES: NC(=O)c1cnc2cncc(N3CCOCC3)c2c1]

a) Ethyl 5-morpholino-1,7-naphthyridine-3-carboxylate

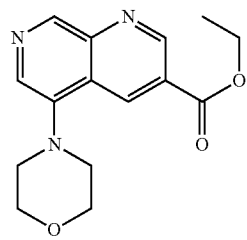 [SMILES: CCOC(=O)c1cnc2cncc(N3CCOCC3)c2c1]

To a suspension of 5-bromo-1,7-naphthyridine-3-carboxylate (500 mg, 1.78 mmol) and palladium (II) acetate (39.9 mg, 178 μmol) and (1,1'-binaphthalene-2,2'-diyl)bis(diphenylphosphine) (BINAP, 222 mg, 356 μmol) and cesium carbonate (1.74 g, 5.34 mmol) in toluene (30 ml) was added morpholine (232 mg, 2.67 mmol). The mixture was stirred at 80 °C. for 15 hours. Removal of the solvent by distillation and chromatography (silica gel, ethyl acetate/heptane=20:80 to 100:0) yielded the title compound as yellow solid (496 mg, 97%). MS: m/e =288.5 [M+H]$^+$.

b) 5-Morpholino-1,7-naphthyridine-3-carboxylic acid

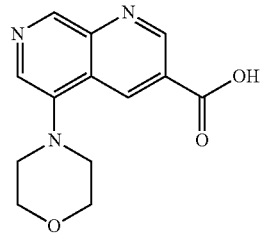 [SMILES: O=C(O)c1cnc2cncc(N3CCOCC3)c2c1]

Ethyl-5-morpholino-1,7-naphthyridine-3-carboxylate (495 mg, 1.72 mmol) was combined with dioxane (20 ml) to give a yellow solution. Lithiumhydroxide (49.5 mg, 2.07 mmol) in water (3 ml) was added and the mixture was stirred at room temperature overnight. The crude reaction mixture was concentrated in vacuo, poured into water (20 ml) and acidified with 2N aqueous hydrochloric acid. The precipitate was dried in vacuo to yield the title compound as yellow solid (415 mg, 93%). MS: m/e=260.4 [M+H]$^+$.

c) 5-Morpholino-1,7-naphthyridine-3-carboxamide

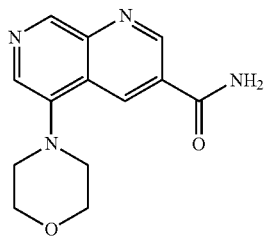

A mixture of 5-morpholino-1,7-naphthyridine-3-carboxylic acid (200 mg, 771 µmol), 1,1'-carbonyldiimidazole (125 mg, 771 µmol) in dichloromethane (15 ml) was stirred at room temperature for 1 hour. Aqueous ammonium hydroxide (25%, 3.0 ml, 77 mol) was added and stirring was continued overnight. Extraction with water/dichloromethane and chromatography (silica gel, ethyl acetate/heptane=40:60 to 100:0 and then preparative HPLC, C18 reverse phase, water (0.1% formic acid)/acetonitrile=80:20 to 98:2) yielded the title compound as off-white solid (7 mg, 4%). MS: m/e=259.4 [M+H]$^+$.

EXAMPLE 17

5-(4-Fluorophenyl)-N-(2,2,2-trifluoroethyl)-1,7-naphthyridine-3-carboxamide

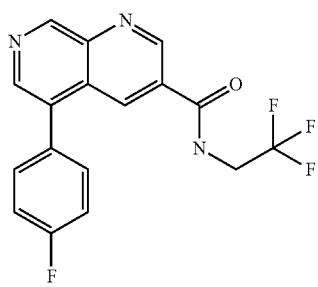

To a suspension of 5-bromo-N-(2,2,2-trifluoroethyl)-1,7-naphthyridine-3-carboxamide (115 mg, 293 µmol) and 4-fluorophenylboronic acid (40.9 mg, 293 µmol) and cesium carbonate (105 mg, 322 µmol) in dioxane (18 ml) and water (1.8 ml) was added bis(diphenylphosphino)ferrocene-palladium(II)dichloride (10.7 mg, 14.6 µmol). The mixture was stirred at 80 °C. for 3 hours. Removal of the solvent by distillation and chromatography (silica gel, ethyl acetate/heptane=50:50 to 100:0) and trituration with diethyl ether/pentane yielded the title compound as off-white solid (45 mg, 44%). MS: m/e=350.4 [M+H]$^+$.

EXAMPLE 18

5-(4-Chlorophenyl)-N-(4-(methylsulfonyl)benzyl)-1,7-naphthyridine-3-carboxamide

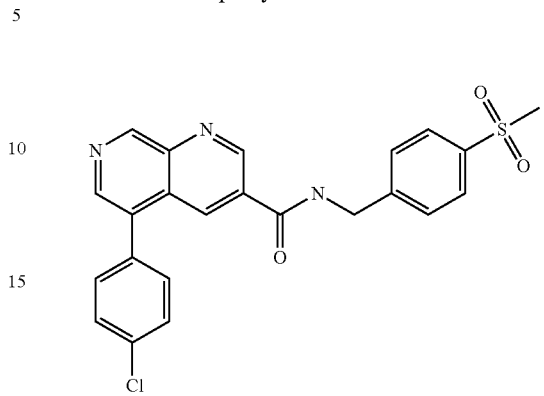

5-(4-Chlorophenyl)-1,7-naphthyridine-3-carboxylic acid (34 mg, 119 µmol) in dichloromethane (10 ml) was combined with 2 drops of dimethylformamide. Oxalyl chloride (75.8 mg, 52.3 µl, 597 µmol) was added slowly at 0° C. The mixture was stirred for 30 minutes at 0° C. and for 30 minutes at room temperature. The crude reaction mixture was concentrated in vacuo. It was taken up in dichloromethane (10 ml) and was added at 0° C. to a mixture of (4-(methylsulfonyl)phenyl)methanamine hydrochloride (26.5 mg, 119 µmol) and triethylamine (37.5 mg, 51.6 µl, 370 µmol) in dichloromethane (10 ml). The mixture was stirred for 30 minutes at 0 ° C. and then at room temperature for 1 hour. Extraction with dichloromethane/water and chromatography (silica gel, ethyl acetate/heptane=50:50 to 100:0) yielded the title compound as off-white solid (25 mg, 46%). MS: m/e=452.4 [M+H]$^+$.

EXAMPLE 19

5-(4-Chlorophenyl)-N-(3-(methylsulfonyl)benzyl)-1,7-naphthyridine-3-carboxamide

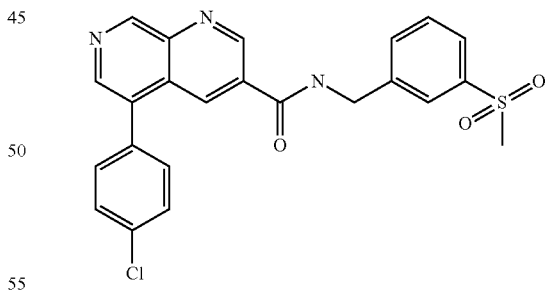

5-(4-Chlorophenyl)-1,7-naphthyridine-3-carboxylic acid (70 mg, 246 µmol) in dichloromethane (20 ml) was combined with 2 drops of dimethylformamide. Oxalyl chloride (156 mg, 108 µl, 1.23 mmol) was added slowly at 0 ° C. The mixture was stirred for 30 minutes at 0 ° C. and for 30 minutes at room temperature. The crude reaction mixture was concentrated in vacuo. It was taken up in dichloromethane (20 ml) and was added at 0 ° C. to a mixture of (3-(methylsulfonyl)phenyl)methanamine (45.5 mg, 246 µmol) and triethylamine (77.1 mg, 106 µl, 762 µmol) in dichloromethane (20 ml). The mixture was stirred for 20 minutes at 0° C. and then at room temperature for 1 hour. Extraction with dichloromethane/water and chromatography (silica gel, ethyl acetate/heptane=50:50 to 100:0) yielded the title compound as off-white solid (62 mg, 56%). MS: m/e=452.3 [M+H]⁺.

EXAMPLE 20

5-(4-Chlorophenyl)-N-(cyclopropylmethyl)-1,7-naphthyridine-3-carboxamide

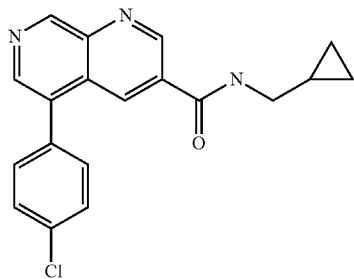

5-(4-Chlorophenyl)-1,7-naphthyridine-3-carboxylic acid (100 mg, 351 µmol) in dichloromethane (30 ml) was combined with 3 drops of dimethylformamide. Oxalyl chloride (223 mg, 154 µl, 1.76 mmol) was added slowly at 0° C. The mixture was stirred for 30 minutes at 0° C. and for 30 minutes at room temperature. The crude reaction mixture was concentrated in vacuo. It was taken up in dichloromethane (30 ml) and was added at 0° C. to a mixture of cyclopropylmethanamine (25.0 mg, 30.5 µl, 351 µmol) and triethylamine (110 mg, 152 µl, 1.09 mmol) in dichloromethane (30 ml). The mixture was stirred for 20 minutes at 0° C. and then at room temperature for 1 hour. Extraction with dichloromethane/water and chromatography (silica gel, ethyl acetate/heptane=50:50 to 100:0) yielded the title compound as off-white solid (111 mg, 94%). MS: m/e=338.4 [M+H]⁺.

EXAMPLE 21

5-(4-Chlorophenyl)-N-(2-methoxyethyl)-1,7-naphthyridine-3-carboxamide

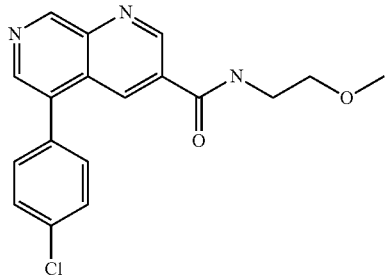 [SMILES: COCCNC(=O)c1cnc2cncc(-c3ccc(Cl)cc3)c2c1]

5-(4-Chlorophenyl)-1,7-naphthyridine-3-carboxylic acid (70 mg, 246 µmol) in dichloromethane (10 ml) was combined with 3 drops of dimethylformamide. Oxalyl chloride (156 mg, 108µl, 1.23 mmol) was added slowly at 0° C. The mixture was stirred for 30 minutes at 0° C. and for 30 minutes at room temperature. The crude reaction mixture was concentrated in vacuo. It was taken up in dichloromethane (20 ml) and was added at 0° C. to a mixture of 2-methoxyethanamine (22.2 mg, 25.4 µl, 295 µmol) and triethylamine (74.6 mg, 103 µl, 738 µmol) in dichloromethane (10 ml). The mixture was stirred for 20 minutes at 0° C. and then at room temperature for 1 hour. Extraction with dichloromethane/water and chromatography (silica gel, ethyl acetate/heptane=50:50 to 100:0) yielded the title compound as off-white solid (71 mg, 85%). MS: m/e=342.4 [M+H]⁺.

EXAMPLE 22

5-(3-Methoxyphenyl)-1,7-naphthyridine-3-carboxamide

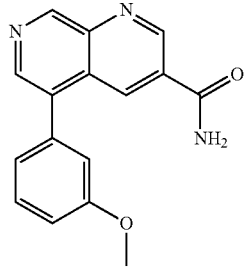

To a suspension of 5-bromo-1,7-naphthyridine-3-carboxamide (60 mg, 238 µmol) and 3-methoxyphenylboronic acid (36.2 mg, 238 µmol) and cesium carbonate (85.3 mg, 262 µmol) in dioxane (5 ml) and water (0.5 ml) was added bis(diphenylphosphino)ferrocene-palladium(II)dichloride (8.71 mg, 11.9 µmol ). The mixture was stirred at 80° C. for 2 hours. Removal of the solvent by distillation and chromatography (silica gel, ethyl acetate) and trituration with diethyl ether/pentane yielded the title compound as off-white solid (60 mg, 90%). MS: m/e=280.4 [M+H]⁺.

EXAMPLE 23

5-(3-(Trifluoromethoxy)phenyl)-1,7-naphthyridine-3-carboxamide

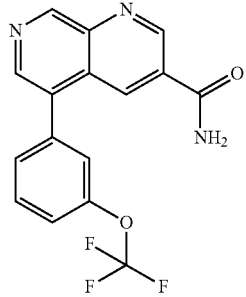 [SMILES: NC(=O)c1cnc2cncc(-c3cccc(OC(F)(F)F)c3)c2c1]

To a suspension of 5-bromo-1,7-naphthyridine-3-carboxamide (60 mg, 238 µmol) and 3-(trifluoromethoxy)phenylboronic acid (49.0 mg, 238 µmol) and cesium carbonate (85.3 mg, 262 µmol) in dioxane (5 ml) and water (0.5 ml) was added bis(diphenylphosphino)ferrocene-palladium(II) dichloride (8.71 mg, 11.9 µmol). The mixture was stirred at 80° C. for 2 hours. Removal of the solvent by distillation and chromatography (silica gel, ethyl acetate) and trituration with diethyl ether/pentane yielded the title compound as off-white solid (68 mg, 86%). MS: m/e=334.4 [M+H]⁺.

EXAMPLE 24

Methyl 3-carbamoyl-1,7-naphthyridine-5-carboxylate

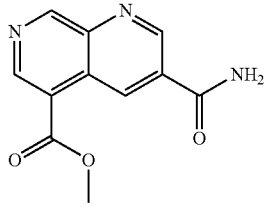 [SMILES: COC(=O)c1cncc2ncc(C(N)=O)cc12]

A solution of 5-bromo-1,7-naphthyridine-3-carboxamide (100 mg, 397 µmol) and triethylamine (80.3 mg, 111 µl, 793 µmol) in methanol (5 ml) and ethyl acetate (5.00 ml) in a steel reactor (35 ml) was combined under argon atmosphere with bis(diphenylphosphino)ferrocene-palladium(II)dichloride (14.5 mg, 19.8 µmol). The reactor was flushed 3 times with carbon monoxide (10 bar) and was then set under carbon monoxide atmosphere (50 bar) and heated to 110° C. After 2 hours the mixture was filtered and concentrated in vacuo to yield the title compound as off-white solid (65 mg, 71%). MS: m/e=232.4 [M+H]⁺.

EXAMPLE 25

5-(3,6-Dihydro-2H-pyran-4-yl)-1,7-naphthyridine-3-carboxamide

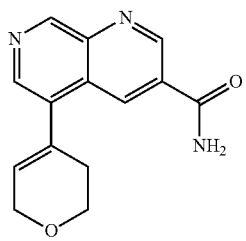 [SMILES: NC(=O)c1cnc2cncc(C3=CCOCC3)c2c1]

To a suspension of 5-bromo-1,7-naphthyridine-3-carboxamide (100 mg, 397 µmol) and 2-(3,6-dihydro-2H-pyran-4-yl)-4,4,5,5-tetramethyl-1,3,2-dioxaborolane (83.3 mg, 397 µmol) and cesium carbonate (142 mg, 436 µmol) in dioxane (3 ml) and water (0.3 ml) was added bis(diphenylphosphino)ferrocene-palladium(II)dichloride (14.5 mg, 19.8 µmol). The mixture was stirred at 80° C. for one hour. Removal of the solvent by distillation and chromatography (silica gel, ethyl acetate/methanol=100:0 to 50:50) yielded the title compound as brown solid (45 mg, 44%). MS: m/e=256.3 [M+H]⁺.

EXAMPLE 26

5-(4,4-Difluoropiperidin-1-yl)-1,7-naphthyridine-3-carboxamide

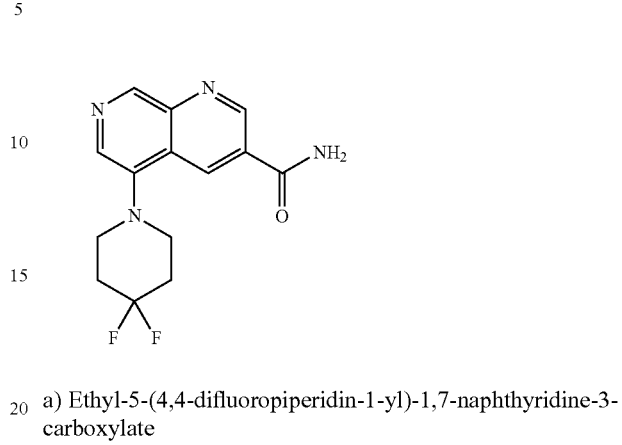

a) Ethyl-5-(4,4-difluoropiperidin-1-yl)-1,7-naphthyridine-3-carboxylate

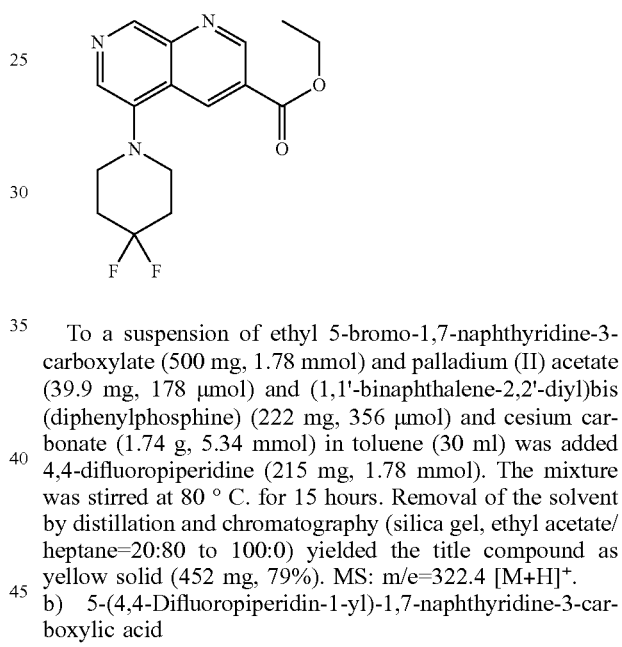

To a suspension of ethyl 5-bromo-1,7-naphthyridine-3-carboxylate (500 mg, 1.78 mmol) and palladium (II) acetate (39.9 mg, 178 µmol) and (1,1'-binaphthalene-2,2'-diyl)bis(diphenylphosphine) (222 mg, 356 µmol) and cesium carbonate (1.74 g, 5.34 mmol) in toluene (30 ml) was added 4,4-difluoropiperidine (215 mg, 1.78 mmol). The mixture was stirred at 80° C. for 15 hours. Removal of the solvent by distillation and chromatography (silica gel, ethyl acetate/heptane=20:80 to 100:0) yielded the title compound as yellow solid (452 mg, 79%). MS: m/e=322.4 [M+H]⁺.

b) 5-(4,4-Difluoropiperidin-1-yl)-1,7-naphthyridine-3-carboxylic acid

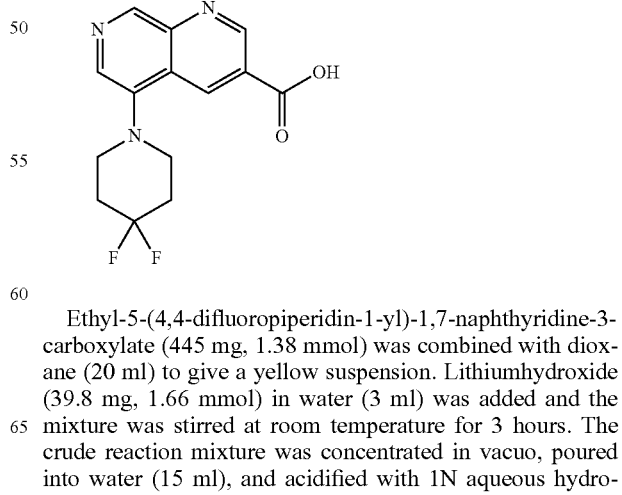

Ethyl-5-(4,4-difluoropiperidin-1-yl)-1,7-naphthyridine-3-carboxylate (445 mg, 1.38 mmol) was combined with dioxane (20 ml) to give a yellow suspension. Lithiumhydroxide (39.8 mg, 1.66 mmol) in water (3 ml) was added and the mixture was stirred at room temperature for 3 hours. The crude reaction mixture was concentrated in vacuo, poured into water (15 ml), and acidified with 1N aqueous hydrochloric acid. The precipitate was filtered and dried to yield the title compound as light yellow solid (285 mg, 70%). MS: m/e=292.5 [M−H]⁻.

c) 5-(4,4-Difluoropiperidin-1-yl)-1,7-naphthyridine-3-carboxamide

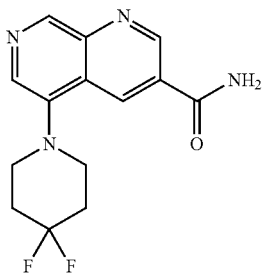

A mixture of 5-(4,4-difluoropiperidin-1-yl)-1,7-naphthyridine-3-carboxylic acid (280 mg, 955 μmol) and 1,1'-carbonyldiimidazole (325 mg, 2.00 mmol) in dichloromethane (20 ml) was stirred at room temperature for 1 hour. Ammonium chloride (255 mg, 4.77 mmol) and triethylamine (483 mg, 665 μl, 4.77 mmol) was added and stirring was continued for 2 hours. Removal of the solvent by distillation and chromatography (silica gel, ethyl acetate/heptane=50:50 to 100:0) yielded the title compound as yellow solid (144 mg, 52%). MS: m/e=293.4 [M+H]⁺.

EXAMPLE 27

5-(6-Chloropyridin-3-yl)-1,7-naphthyridine-3-carboxamide

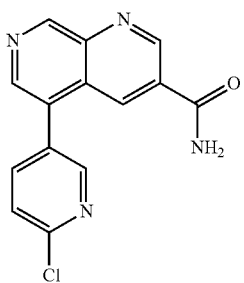

To a suspension of 5-bromo-1,7-naphthyridine-3-carboxamide (70 mg, 278 μmol) and 6-chloropyridin-3-ylboronic acid (43.7 mg, 278 μmol) and cesium carbonate (99.5 mg, 305 μmol) in dioxane (10 ml) and water (1.0 ml) was added bis(diphenylphosphino)ferrocene-palladium(II)dichloride (10.2 mg, 13.9 μmol). The mixture was stirred at 80° C. overnight. Removal of the solvent by distillation and chromatography (silica gel, ethyl acetate) yielded the title compound as off-white solid (65 mg, 82%). MS: m/e=285.4 [M+H]⁺.

EXAMPLE 28

5-(2,4-Dichlorophenyl)-1,7-naphthyridine-3-carboxamide

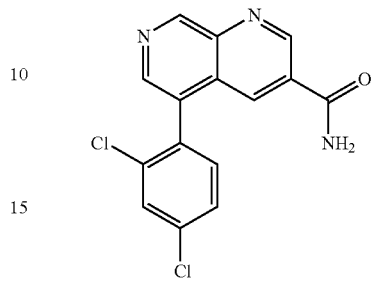

To a suspension of 5-bromo-1,7-naphthyridine-3-carboxamide (70 mg, 278 μmol) and 2,4-dichlorophenylboronic acid (53.0 mg, 278 μmol) and cesium carbonate (99.5 mg, 305 μmol) in dioxane (10 ml) and water (1.0 ml) was added bis(diphenylphosphino)ferrocene-palladium(II)dichloride (10.2 mg, 13.9 μmol). The mixture was stirred at 80° C. overnight. Removal of the solvent by distillation and chromatography (silica gel, ethyl acetate) yielded the title compound as white solid (79 mg, 90%). MS: m/e =318.3 [M+H]⁺.

We claim:
1. A compound of formula I

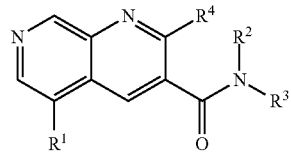

wherein
R¹ is phenyl or pyridinyl, which are optionally substituted by one, two or three substituents, selected from halogen, lower alkyl substituted by halogen, lower alkoxy, lower alkoxy substituted by halogen, cyano or S(O)₂-lower alkyl, or is
morpholinyl, dihydropyranyl or piperidinyl, wherein piperidinyl is optionally substituted by halogen, or is C(O)O-lower alkyl;
R² is hydrogen;
R³ is hydrogen, lower alkyl substituted by halogen, —(CH₂)ₙ—S(O)₂-lower alkyl, —(CH₂)ₙ-cycloalkyl or —(CH₂)ₙ-lower alkoxy;
R⁴ is hydrogen or lower alkyl;
n is 0, 1 or 2;
or a pharmaceutically acceptable acid addition salt, a racemic mixture or its corresponding enantiomer and/or optical isomers thereof.

2. The compound of formula I according to claim 1, wherein R¹ is phenyl or pyridinyl, which are optionally substituted by one, two or three substituents, selected from halogen, lower alkyl substituted by halogen, lower alkoxy, lower alkoxy substituted by halogen, cyano or S(O)₂-lower alkyl.

3. The compound of claim 1 which compounds are:
5-(4-chlorophenyl)-1,7-naphthyridine-3-carboxamide;

5-(4-(trifluoromethoxy)phenyl)-1,7-naphthyridine-3-carboxamide;
5-(2-fluorophenyl)-1,7-naphthyridine-3-carboxamide;
5-(3,4,5-trifluorophenyl)-1,7-naphthyridine-3-carboxamide;
5-(4-fluorophenyl)-1,7-naphthyridine-3-carboxamide;
5-(3,4-difluorophenyl)-1,7-naphthyridine-3-carboxamide;
5-(2,4-difluorophenyl)-1,7-naphthyridine-3-carboxamide;
5-(4-cyanophenyl)-1,7-naphthyridine-3-carboxamide;
5-(4-(methylsulfonyl)phenyl)-1,7-naphthyridine-3-carboxamide;
5-(4-(trifluoromethyl)phenyl)-1,7-naphthyridine-3-carboxamide;
5-(4-chlorophenyl)-2-methyl-1,7-naphthyridine-3-carboxamide;
5-(4-chloro-2-fluorophenyl)-1,7-naphthyridine-3-carboxamide;
5-(4-chloro-2-fluorophenyl)-N-(2-(methylsulfonyl)ethyl)-1,7-naphthyridine-3-carboxamide;
5-(2-fluorophenyl)-N-(2,2,2-trifluoroethyl)-1,7-naphthyridine-3-carboxamide;
5-(2,4-difluorophenyl)-N-(2,2,2-trifluoroethyl)-1,7-naphthyridine-3-carboxamide;
5-(4-fluorophenyl)-N-(2,2,2-trifluoroethyl)-1,7-naphthyridine-3-carboxamide;
5-(4-chlorophenyl)-N-(4-(methylsulfonyl)benzyl)-1,7-naphthyridine-3-carboxamide;
5-(4-chlorophenyl)-N-(3-(methylsulfonyl)benzyl)-1,7-naphthyridine-3-carboxamide;
5-(4-chlorophenyl)-N-(cyclopropylmethyl)-1,7-naphthyridine-3-carboxamide;
5-(4-chlorophenyl)-N-(2-methoxyethyl)-1,7-naphthyridine-3-carboxamide;
5-(3-methoxyphenyl)-1,7-naphthyridine-3-carboxamide;
5-(3-(trifluoromethoxy)phenyl)-1,7-naphthyridine-3-carboxamide;
5-(6-chloropyridin-3-yl)-1,7-naphthyridine-3-carboxamide; or,
5-(2,4-dichlorophenyl)-1,7-naphthyridine-3-carboxamide.

4. The compound of claim 1, wherein $R^1$ is morpholinyl, dihydropyranyl or piperidinyl, wherein piperidinyl is optionally substituted by halogen.

5. The compound of claim 1, which compounds are:
5-morpholino-1,7-naphthyridine-3-carboxamide;
methyl 3-carbamoyl-1,7-naphthyridine-5-carboxylate;
5-(3,6-dihydro-2H-pyran-4-yl)-1,7-naphthyridine-3-carboxamide; or,
5-(4,4-difluoropiperidin-1-yl)-1,7-naphthyridine-3-carboxamide.

6. The compound of claim 1, wherein $R^2$ and $R^3$ are both hydrogen.

7. The compound of claim 1 which compounds are:
5-(4-chlorophenyl)-1,7-naphthyridine-3-carboxamide;
5-(4-(trifluoromethoxy)phenyl)-1,7-naphthyridine-3-carboxamide;
5-(2-fluorophenyl)-1,7-naphthyridine-3-carboxamide;
5-(3,4,5-trifluorophenyl)-1,7-naphthyridine-3-carboxamide;
5-(4-fluorophenyl)-1,7-naphthyridine-3-carboxamide;
5-(3,4-difluorophenyl)-1,7-naphthyridine-3-carboxamide;
5-(2,4-difluorophenyl)-1,7-naphthyridine-3-carboxamide;
5-(4-cyanophenyl)-1,7-naphthyridine-3-carboxamide;
5-(4-(methylsulfonyl)phenyl)-1,7-naphthyridine-3-carboxamide
5-(4-(trifluoromethyl)phenyl)-1,7-naphthyridine-3-carboxamide;
5-(4-chlorophenyl)-2-methyl-1,7-naphthyridine-3-carboxamide;
5-(4-chloro-2-fluorophenyl)-1,7-naphthyridine-3-carboxamide;
5-morpholino-1,7-naphthyridine-3-carboxamide;
5-(3-methoxyphenyl)-1,7-naphthyridine-3-carboxamide;
5-(3-(trifluoromethoxy)phenyl)-1,7-naphthyridine-3-carboxamide;
methyl 3-carbamoyl-1,7-naphthyridine-5-carboxylate;
5-(3,6-dihydro-2H-pyran-4-yl)-1,7-naphthyridine-3-carboxamide;
5-(4,4-difluoropiperidin-1-yl)-1,7-naphthyridine-3-carboxamide;
5-(6-chloropyridin-3-yl)-1,7-naphthyridine-3-carboxamide; or,
5-(2,4-dichlorophenyl)-1,7-naphthyridine-3-carboxamide.

8. A process for the manufacture of a compound of formula I as defined in claim 1 which process comprises
a) reacting a compound of formula (I-A)

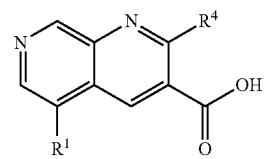

with a compound of formula $NHR^2R^3$ (2) to afford a compound of formula (I)

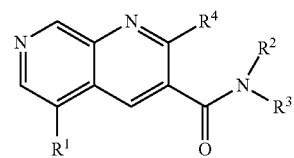

and, optionally, converting the compounds obtained into pharmaceutically acceptable acid addition salts, or
a) reacting a compound of formula 3

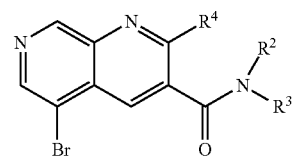

with a compound of formula $(HO)_2B—R^1$ (4)
to afford a compound of formula I and, optionally, converting the compounds obtained into pharmaceutically acceptable acid addition salts.

9. A pharmaceutical composition comprising a compound of claim 1 and at least one pharmaceutically acceptable excipients, diluents or carrier.

10. A method for the treatment of depression, anxiety disorders, Parkinson's disease, Alzheimer's disease, amyotrophic lateral sclerosis, stroke, comprising administering to a patient in need thereof a therapeutically effective amount of a compound of claim 1.

11. A method for modulating neurogenesis of neural stem cells comprising treatment said stem cells with a compound according to claim 1.

* * * * *